(12) United States Patent
Araya et al.

(10) Patent No.: US 9,044,595 B2
(45) Date of Patent: Jun. 2, 2015

(54) SYSTEM AND METHOD FOR REDUCING LIPID CONTENT OF ADIPOCYTES IN A BODY

(71) Applicant: Heidi Araya, Orlando, FL (US)

(72) Inventors: Heidi Araya, Orlando, FL (US); Terry J. Ward, Orlando, FL (US)

(*) Notice: Subject to any disclaimer, the term of this patent is extended or adjusted under 35 U.S.C. 154(b) by 47 days.

(21) Appl. No.: 13/784,166

(22) Filed: Mar. 4, 2013

(65) Prior Publication Data

US 2013/0268035 A1    Oct. 10, 2013

Related U.S. Application Data

(60) Provisional application No. 61/606,628, filed on Mar. 5, 2012.

(51) Int. Cl.
*A61N 5/06*    (2006.01)

(52) U.S. Cl.
CPC ....... *A61N 5/0613* (2013.01); *A61N 2005/0642* (2013.01); *A61N 2005/0652* (2013.01)

(58) Field of Classification Search
CPC ............ A61N 5/06; A61B 18/18; A61B 5/00; A61B 5/02; G08B 23/00
USPC .............. 607/88, 89, 92; 606/9, 2; 340/573.1; 600/340, 483
See application file for complete search history.

(56) References Cited

U.S. PATENT DOCUMENTS

| | | | | |
|---|---|---|---|---|
| 4,646,743 A | * | 3/1987 | Parris | 607/92 |
| 4,803,625 A | * | 2/1989 | Fu et al. | 600/483 |
| 6,013,096 A | * | 1/2000 | Tucek | 607/89 |
| 6,290,713 B1 | * | 9/2001 | Russell | 607/88 |
| 6,350,275 B1 | * | 2/2002 | Vreman et al. | 607/88 |
| 6,602,245 B1 | * | 8/2003 | Thiberg | 606/2 |
| 6,602,275 B1 | * | 8/2003 | Sullivan | 607/88 |
| 6,615,065 B1 | * | 9/2003 | Barrett et al. | 600/340 |
| 7,198,624 B2 | * | 4/2007 | Muzzi et al. | 606/9 |
| 7,364,583 B2 | | 4/2008 | Rose | |
| 7,482,935 B2 | * | 1/2009 | Lee | 340/573.1 |

(Continued)

FOREIGN PATENT DOCUMENTS

WO    WO 0050807 A1 * 8/2000

OTHER PUBLICATIONS

Efficacy of Low-Level Laser Therapy. Caruso-Davis MK et al. Greenway FL, School of Human Ecology, Louisiana State University. Obes Surg. Apr. 15, 2010.*

(Continued)

*Primary Examiner* — William Thomson
*Assistant Examiner* — Vicor Shapiro
(74) *Attorney, Agent, or Firm* — Terry M. Sanks, Esq.; Cian G. O'Brien, Esq.; Beusse Wolter Sanks & Maire, P.A.

(57) ABSTRACT

A system is provided for reducing lipid content of adipocytes in a body. The system includes an optical device configured to illuminate a region of the body at a selective peak wavelength and at a selective power density for a selective time period. The system also includes a controller connected to the optical device to determine the selective wavelength, the selective power density and the selective time period to stimulate lipolysis in the adipocytes. A system is also provided for reducing pain in the body. A method is also provided for reducing lipid content of adipocytes in the body.

21 Claims, 4 Drawing Sheets

(56) References Cited

U.S. PATENT DOCUMENTS

| | | | |
|---|---|---|---|
| 7,559,945 B2 * | 7/2009 | Breden et al. | 607/88 |
| 2002/0082528 A1 * | 6/2002 | Friedman et al. | 601/2 |
| 2003/0045916 A1 * | 3/2003 | Anderson et al. | 607/89 |
| 2005/0049582 A1 * | 3/2005 | DeBenedictis et al. | 606/9 |
| 2005/0075703 A1 | 4/2005 | Larsen | |
| 2006/0064144 A1 | 3/2006 | Chen et al. | |
| 2007/0197884 A1 | 8/2007 | Bornstein | |
| 2007/0239075 A1 * | 10/2007 | Rosenberg et al. | 601/2 |
| 2008/0119912 A1 | 5/2008 | Hayes | |
| 2008/0275533 A1 | 11/2008 | Powell | |
| 2009/0222068 A1 | 9/2009 | Oberreiter et al. | |
| 2010/0016931 A1 * | 1/2010 | Shanks et al. | 607/89 |
| 2012/0030872 A1 | 2/2012 | Turtzo | |
| 2014/0249607 A1 | 9/2014 | Ward | |

OTHER PUBLICATIONS

Electronics a device that responds to a small current or voltage. The American Heritage® Dictionary of the English Language, Fourth Edition copyright © 2000 Updated in 2009. Published by Houghton Mifflin Company.*

International Search Report: Jun. 20, 2013.

* cited by examiner

SYSTEM AND METHOD FOR REDUCING LIPID CONTENT OF ADIPOCYTES IN A BODY

CROSS-REFERENCE TO RELATED APPLICATIONS

This application claims the benefit of U.S. Provisional Patent Application No. 61/606,628 filed Mar. 5, 2012, which is incorporated herein by reference.

FIELD OF THE INVENTION

The present invention relates to medical devices, and more particularly, to medical devices for reducing fat content in a body and improving physical appearance. Even more particularly, the present invention relates to medical devices using phototherapy to improve appearance of the human body by reduction of body fat content.

BACKGROUND OF THE INVENTION

To reduce fat in the human body, behavior modification has been a conventional method with minimal risk to the patient. However, behavior modification involves a high rate of recidivism and noncompliance where the patient frequently reverts back to his or her former eating and lifestyle patterns. Thus, long term success is only moderately successful. Furthermore, short term weight loss in patients is frequently followed by weight gain and thus results in a difficulty in remaining a normal and healthy weight. Additionally, pharmacological methods have been used to reduce body fat, which rely on reducing feelings of hunger or reducing absorption of nutrients. This method has also shown to have limited effectiveness, in addition to causing side effects.

Other conventional methods to reduce fat in the human body involve surgical methods such as liposuction (suction lipectomy) which are inherently risky and invasive by potentially damaging surrounding tissue, nerves, skin, as well as potentially causing pain, trauma and infection. Additionally, these surgical methods are typically only effective with localized subcutaneous adipose deposits.

Other recently-approved devices by the Food and Drug Administration (FDA) to reduce fat in the human body include devices utilizing cryogenics to freeze fat cells, after which the fat cells die and are metabolized by the body. These devices involve inherent drawbacks, such as delayed results, which may not be realized for up to four months, and an inherent risk of damage to surrounding tissue in a vicinity of the fat cells.

BRIEF DESCRIPTION OF THE INVENTION

In one embodiment of the present invention, a system is provided for reducing lipid content of adipocytes in a body. The system includes an optical device configured to illuminate a region of the body at a selective peak wavelength and at a selective power density for a selective time period. The system further includes a controller connected to the optical device to determine the selective wavelength, the selective power density and the selective time period to stimulate lipolysis in the adipocytes.

In another embodiment of the present invention, a system is provided for pain reduction in a body. The system includes a support to hold a region of the body and an array of LEDs configured to output a peak wavelength with a selective power density at the region of the body for a selective time period sufficient to reduce pain in the region of the body. The system also includes a stand to hold the array of LEDs at a selective distance above the region of the body. The system also includes a controller connected to the LEDs and the stand. The controller is configured to transmit a signal to the stand or the support to vary the selective distance of the LEDs above the region of the body and to modulate an output of the LEDs at a selective frequency. The controller is configured to modulate the output of the LEDs based on a transmission of an input signal to the LEDs at the selective frequency based on one of an internal modulation signal or an external modulation signal.

In another embodiment of the present invention, a method is provided for reducing lipid content of adipocytes in a body. The method begins by positioning a region of the body on a support. The method then involves determining a selective peak wavelength of radiation from an optical device to the region of the body to stimulate lipolysis in the adipocytes in the region of the body. The method then involves determining a selective power density of radiation at the region of the body to stimulate lipolysis in the adipocytes, including varying a selective distance between the optical device and the region of the body. The method then involves determining a selective time period to transmit the radiation from the optical device to the region of the body. The determining of the selective time period step is based on the step of varying the selective distance between the optical device and the region of the body. Then method then involves illuminating the region of the body with radiation from the optical device at the selective peak wavelength and with the selective power density at the region of the body for the selective time period to stimulate lipolysis in the adipocytes in the region of the body. The illuminating step includes modulating the radiation at a selective frequency.

BRIEF DESCRIPTION OF THE DRAWINGS

A more particular description of the invention briefly described above will be rendered by reference to specific embodiments thereof that are illustrated in the appended drawings. Understanding that these drawings depict only typical embodiments of the invention and are not therefore to be considered to be limiting of its scope, the embodiments of the invention will be described and explained with additional specificity and detail through the use of the accompanying drawings in which.

DETAILED DESCRIPTION OF THE INVENTION

In describing particular features of different embodiments of the present invention, number references will be utilized in relation to the figures accompanying the specification. Similar or identical number references in different figures may be utilized to indicate similar or identical components among different embodiments of the present invention.

Figure 1:
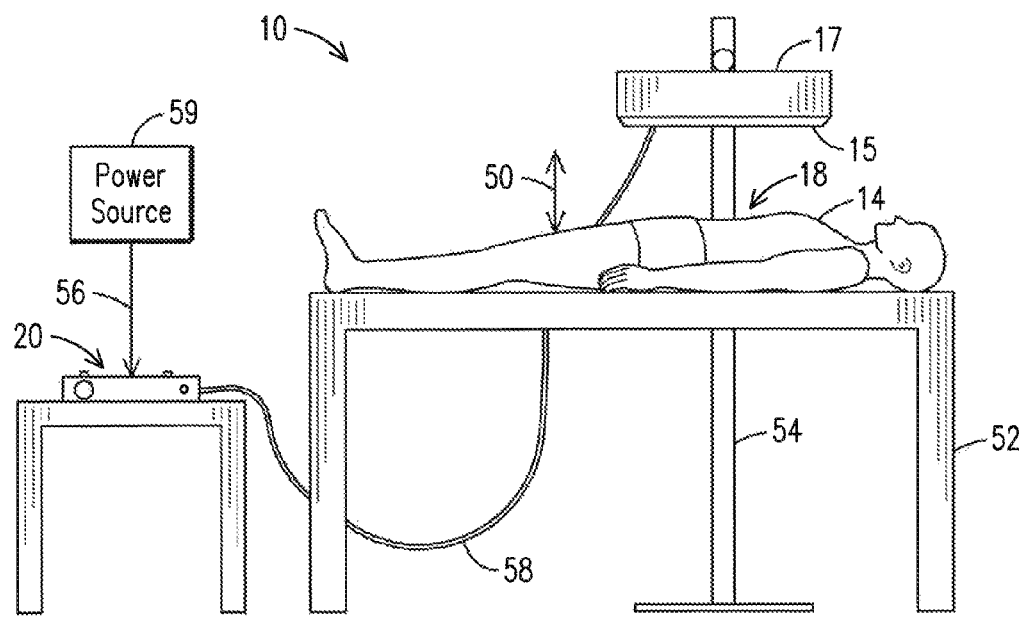
FIG. 1 is a side view of a system for reducing lipid content of adipocytes in a body in accordance with the present invention.

The inventor of the present invention recognized that conventional methods for reducing lipid content in adipocytes involved either delayed results (up to four months), possible damage to surrounding adipocyte tissue and/or were restricted to overweight (not obese) patients. Thus, the inventor developed a system and method for reducing lipid content in patients, irrespective of whether the patient is overweight or obese, in which results are achieved in a much shorter time span than the conventional methods and in which no damage is caused to surrounding adipocyte tissue or any other tissue. The inventor of the present invention developed the system which may cause one or more small pores to open in adipocytes for a short period, such as of approximately 48-72 hours, for example, during which lipid content is emptied and metabolized from the adipocytes. The liberated lipid content from the adipocytes is then drained by the lymphatic system and processed by the liver as part of the body's normal course of detoxification. The inventor of the present invention recognized that results in the system of the present invention were optimal in those individuals who limited fat intake during the treatment, minimized or avoided intake of alcohol, performed moderate exercise and stayed hydrated by drinking a sufficient quantity of water during the treatment. Although these factors may affect the degree of results for certain patients, they are not required factors in order for results to be obtained in patients. FIG. 1 illustrates a system 10 for reducing lipid content of adipocytes 12 in a body 14 and/or for reducing pain in the body 14. Although the system 10 will be discussed below, with reference to the effect of reducing lipid content of adipocytes 12 in the body 14, the system 10 may have an additional benefit of reducing pain in the body 14. Thus, the structural features of the system 10 discussed below, with reference to the effect of reducing lipid content of adipocytes 12 in the body 14 are restated herein with respect to the system 10 being used for the additional benefit of reducing pain in the body 14. Indeed, the system 10 reduces the quantity of lipids in the adipocytes 12 without adverse effects to the adipocytes 12, to the irradiated skin, or to the surrounding tissue. The system 10 stimulates various biochemical processes which include, but are not limited to, pain reduction, shortening of healing time, and scar reduction, as well as lipolysis and collagen and elastin stimulation. Additionally, collagen and elastin stimulation may complement the lipolysis, since weight loss may cause the skin to sag and create stretch marks. Collagen and elastin stimulation mitigate the instances of sagging skin and stretch marks due to the weight loss based on lipolysis. Upon reducing the lipid content from the adipocytes 12, metabolism of the freed lipids may be needed for successful weight loss, and thus individuals who are unable to adequately metabolize lipids using normal bodily functions (i.e., liver), may not be suitable for treatment with the system 10. However, even such individuals may still benefit from other advantages of the system 10, as discussed below.

As illustrated in FIG. 1, the system 10 includes an optical device, such an as LED array 15 that is provided within a housing 17, and is configured to illuminate a region 18 of the body 14 at a selective peak wavelength and at a selective power density for a selective time period, in order to stimulate lipolysis in adipocytes 12 at the region 18 of the body 14. The region 18 of the body 14 is determined by the patient's desire to lose fat from the body 14 in that region 18. Exemplary regions 18 of the body 14 may include, but are not limited to: breasts, the waist, the lower back, the upper thighs, and/or the neck, for example. As further illustrated in FIG. 1, the system 10 also includes a controller 20 that is connected to the housing 17 of the LED array 15 with a cable 58. The controller 20 is used to determine the selective peak wavelength of the radiation from the LED array 15, the selective power density of the radiation at the region 18 of the body 14, and the selective time period to illuminate the region 18 of the body 14, so that lipolysis is stimulated in adipocytes 12 at the region 18 of the body 14. In an exemplary embodiment, the controller 20 determines the selective peak wavelength from a range of 630-660 nm; the controller 20 determines the selective power density from a range between 75-1500 $mW/cm^2$; and the controller 20 determines the selective time period from a range between 5-120 minutes. One factor which determines which wavelength is selected by the controller 20 within the wavelength range of 630-660 nm is whether collagen and elastin stimulation, pain reduction or lipolysis is to be performed at the region 18 of the body 14. For example, if lipolysis is to be performed at the region 18 of the body 14, the controller 20 selects the peak wavelength from a narrower wavelength range, such as between 630-650 nm, for example. In another example, if collagen and elastin stimulation or pain reduction is to be performed at the region 18 of the body 14, the controller 20 selects the peak wavelength from a broader wavelength range, such as 630-660 nm, for example. In an additional exemplary embodiment, the controller 20 determines a selective energy density of the radiation from the LED array 15 at the region 18 of the body 14 from a range between 4-82.5 J/cm2. Depending on whether the LED array 15 is being used to stimulate elastin and collagen, reduce pain or for lipolysis, the controller 20 is configured to select the appropriate energy density within the range. For example, the stimulation of collagen or reduction of pain in the region 18 of the body 14 has a lower energy density threshold than lipolysis and thus takes place at a smaller energy density than lipolysis. Thus, the controller 20 is configured to select a smaller energy density during the stimulation of collagen and a higher energy density from the above energy density range during lipolysis within the region 18 of the body 14. In another exemplary embodiment, the selective time period may be determined within a range between 15-100 minutes. In another exemplary embodiment, the controller 20 determines the selective peak wavelength to be 635 nm, and the controller 20 determines the selective time period from a range between 5-40 minutes. In an additional exemplary embodiment, the controller 20 determines the selective wavelength, the selective power density and the selective time period in order to stimulate lipolysis in the adipocytes 12 of the region 18 of the body 14 where the body 14 has a body mass index (BMI) in excess of an obese BMI threshold. For example, the BMI of the body 14 is in excess of 30. However, the system 10 of the present invention is not limited to being used with a body having any specific BMI and may be used to stimulate lipolysis in adipocytes in a body having a BMI less than or greater than 30. The selective power density, determined within the above range of 75-1500 $mW/cm^2$, is used to create a reaction in the adipocytes 12 and may vary in effect on each body 14 depending on a thickness of the adipocytes 12 in each body 14. The selective power density in the above range is sufficient to stimulate lipolysis by encouraging an emptying of the adipocytes 12 into interstitial space, where the lipid content is metabolized using normal bodily processes.

Additionally, as illustrated in FIG. 1, the system 10 includes a support such as a table 52 to hold the body 14, and an adjustable stand 54 to hold the LED array 15 at a selective distance 50 above the body 14. In an exemplary embodiment, the stand 54 includes a swingable arm which can be raised or lowered manually and tightened in place, to adjust the selective distance 50. However, the adjustable stand 54 may include a motor which is powered by a signal from the controller 20, to adjustably move the LED array 15 up or down, and correspondingly adjust the selective distance 50, for example. The controller 20 is connected to the adjustable stand 54 with the cable 58, so that the controller 20 transmits the signal to the adjustable stand 54 to vary the selective distance 50. When the controller 20 varies the selective distance 50, the controller 20 correspondingly adjusts the selective time period, in order to deliver an equivalent amount of energy to the region 18 of the body 14 over the selective time period. Although the embodiment of FIG. 1 discusses the arrangement of the table 52 and the adjustable stand 54, the embodiments of the present invention are not limited to this arrangement and may include a fixed stand and any type of support, including an adjustable support, to hold the patient, which receives a signal from the controller 20, in order to move up or down, to vary the selective distance. Additionally, although FIG. 1 illustrates that the table is used to hold all of the patient's body 14, the embodiments of the present invention are not limited to this arrangement, and may feature any type of support which is configured to hold just the region 18 of the patient's body 14 that is subject to the treatment with the system 10, for example.

In an exemplary embodiment, for each treatment with the system 10, the user employs input features of the controller 20 to adjust the selective time period and the selective distance 50, so that during the treatment the LED array 15 illuminates the region 18 of the body 14 at the selective distance 50 for the selective time period. The patient may undergo multiple treatments by the system 10 in one day, in which the same region 18 of the body 14 is treated by the system 10 or in which multiple regions of the body 14 are treated by the system, by moving either the stand 54 or the patient in between treatments. If the patient undergoes multiple treatments by the system 10 in one day, the system 10 may include a maximum total time period during which the patient can be treated during the day, to ensure that the patient's body has adequate time to metabolize the lipid content emptied from the adipocytes 12 during the total time period. Additionally, the system 10 may include a minimum rest period, between the days that the patient undergoes treatment for the maximum total time period. The minimum rest period should be long enough so that the body 14 has adequate time to metabolize the released lipid content from the adipocytes 12 during the treatment(s), but the minimum rest period should also be short enough so that the pores of the adipocytes 12 opened by the treatment are still open during a subsequent treatment. As previously discussed, the pores of the adipocytes 12 at the region 18 of the body 14 may be open for approximately 48-72 hours after treatment by the system 10, for example. In an exemplary embodiment, the radiation from the LED array 15 causes the mitochondria in the nucleus of the adipocytes 12 to open transitory pores in the cell membranes of the adipocytes 12. For example, the system 10 may limit the maximum total time period during which a patient can be treated during a day to 48 minutes. In another example, the system 10 may limit the maximum total time period that the patient can be treated to 48 minutes, and provide a minimum rest period of one day, so that the patient can undergo the 48 minute treatment period every other day, for example. For example, a patient may undergo 6 individual 8 minute treatments in one day, with one day rest period in between. In another example, the patient may undergo 3 individual 16 minute treatments in one day, with one day rest period in between. The maximum total time period and the minimum rest period may be stored in a memory of the controller 20 along with patient identifying information, and the controller 20 may feature an internal clock so that the controller 20 can track whether a specific patient is eligible for treatment, for example. Depending on what region 18 of the patient's body 14 is to be treated, multiple treatments in one day may or may not be necessary. For example, if a patient seeks to lose weight around a thigh region 18 of the body 14, the system 10 may be used to perform multiple treatments on different portions of the thigh region 18 of the body 14, where the patient rotates different portions of the thigh region of the body 14 to the LED array 15 in between each treatment, for example. In another example, if the patient seeks to lose weight from a lower back region of the body 14, the system 10 may not need to perform multiple treatments on the lower back region.

In an exemplary embodiment, upon reducing the selective distance 50, the controller 20 reduces the selective time period. In another exemplary embodiment, upon increasing the selective distance 50, the controller 20 increases the selective time period. Thus, when the power density at the region 18 is lowered by raising of the LED array 15 away from the region 18 of the body 14, the controller 20 may increase the selective time period for more optimal results and when the power density at the region 18 is raised by lowering the LED array 15 closer to the region 18 of the body 14, the controller 20 may decrease the selective time period, for more optimal results. In an exemplary embodiment, the controller 20 adjusts the adjustable stand 54 so that the selective distance 50 is approximately 8 inches, and adjusts the selective time period to approximately 8 minutes for each treatment, for example. For this exemplary embodiment (selective distance is approximately 8 inches and the selective time period is approximately 8 minutes) the above-discussed maximum total time period of 48 minutes and minimum rest period of one day may also be used. In the exemplary embodiment, the LED array 15 is configured to collectively output 300 watts through the LEDs 16 at the selective distance 50 of approximately 8 inches, in order to establish a sufficient energy power density at the region 18 of the body 14 which stimulates lipolysis in the adipocytes 12. In an exemplary embodiment, when the selective distance 50 is set at approximately 8 inches, the LED array 15 is configured to illuminate the region 18 (within the adipose tissue layer 46) that spans an area of approximately 43.1 cm×53.3 cm, for example, in order to establish the sufficient energy power density at the region 18 to stimulate lipolysis in the adipocytes 12. Thus, in the above exemplary embodiment, a patient may undergo multiple 8-minute long treatments, provided that the patient does not undergo more than 48 minutes of total treatment time, every other day, thus providing the patient's body with adequate time to metabolize the emptied lipid content from the adipocytes 12. Indeed, the controller 20 maintains the selective distance 50 to be no greater than a maximum distance, since if the LED array 15 is raised too far above the region 18 of the body 14, the LED array 15 illuminates the region 18 with an insufficient energy density for lipolysis of the adipocytes 12. If a patient seeks to remove visceral fat from the region 18 of the body 14, the controller 20 may adjust the selective distance 50 to be less than if a patient seeks to remove subcutaneous fat from the region 18 of the body 14. In an exemplary embodiment, the selective distance 50 may be moved within a range of 1 inch to 18 inches, for example. However, the selective distance is not limited to this specific range and may be adjusted to a distance outside this range, provided that the LED array 15 effectively reduces the lipid content in the adipocytes at the region of the body.

Figure 2:
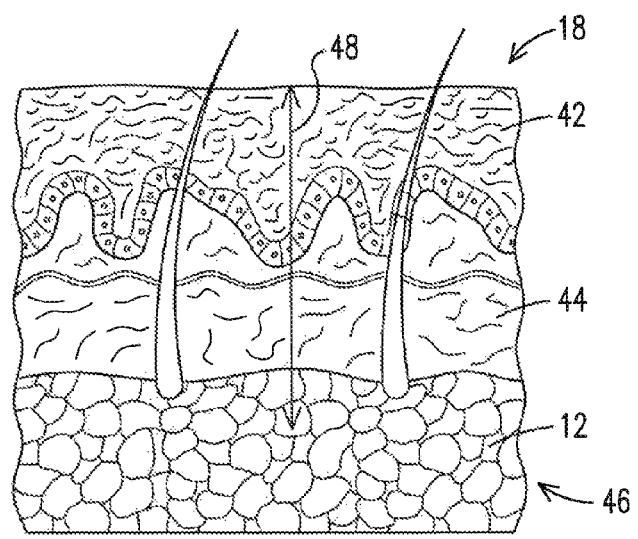
FIG. 2 is a cross-sectional side view of a region of the body treated with the system of FIG. 1.

FIG. 2 illustrates the region 18 of the body 14 discussed above, including an epidermis layer 42, a dermis layer 44 and an underlying adipose tissue layer 46 with the adipocytes 12 in which the system 10 is used to simulate lipolysis. As illustrated in FIG. 2, the radiation from the LED array 15 is configured to penetrate through the epidermis layer 42, the dermis layer 44 and to the adipocytes 12 in the adipose tissue layer 46 at a depth range between 8-10 mm, for example. Lipolysis of the adipocytes 12 in the adipose tissue layer 46 occurs once the LED array 15 delivers a sufficient energy density (J/cm2) to the adipose tissue layer 46 at the region 18 of the body 14. The lipolysis of the adipocytes 12 is specific to the adipose tissue layer 46 at the region 18 of the body 14, but may be transmitted to other regions of the body 14 outside of the region 18. However, this numeric depth range is not limiting and the system 10 may provide an LED array which is configured to penetrate a depth which is less or greater than this depth range, provided that the penetrated depth is sufficient to stimulate lipolysis in the adipocytes in the region of the body. In an exemplary embodiment, selection of the peak wavelength from the range between 630-660 nm is to stimulate natural intracellular photochemical processes which in turn reduce pain and stimulate the body's production of collagen and elastin. If the patient seeks to reduce pain at the region 18 of the body 14 (rather than remove fat through lipolysis), then the selective time period may be adjusted to a longer period than the selective time period used for lipolysis. For example, a selective time period used for pain reduction may be 20 minutes, which is longer than the above-discussed exemplary selective time period of 8 minutes that is used for lipolysis. The dermis layer 44 elasticity is due to the presence of elastin fibers. Thus, increasing collagen and elastin production will improve the skin's appearance so that it appears smoother, tighter and reduce fine lines and wrinkles. In addition, other advantages of using a selective peak wavelength in the range between 630-660 nm include diminishment of wrinkles and fine lines; improvement in skin tone and texture; refinement of large pores; lightening of age spots; lightening of dark under eye circles; improvement in overall evenness of skin tone; treatment of acne spots; enhancement of Adenosine triphosphate (ATP) production in the mitochondria, which provides more energy substrate for cellular healing and tissue recovery post injury; and decreasing inflammatory mediators in wounds and increasing endogenous endorphin release. However, the present invention is not limited to the use of a selective peak wavelength in this specific range or for these specific advantages, and may include selection of any selective peak wavelength, provided that the use of this selective peak wavelength reduces the lipid content of the adipocytes 12 at the body region 18.

Figure 3:
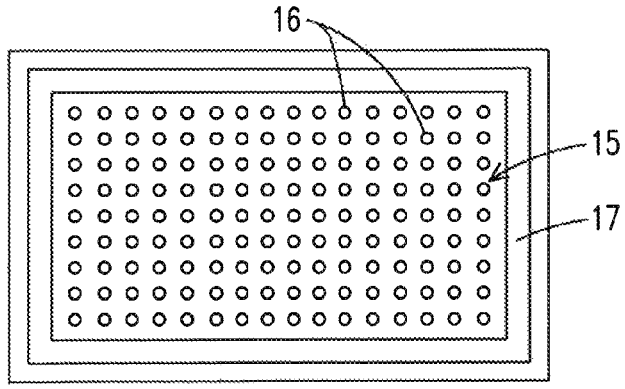
FIG. 3 is a plan view of an array of LEDs used in the system of FIG. 1.

FIG. 3 illustrates the housing 17 of the LED array 15, which includes a rectangular grid of LEDs 16. In the exemplary embodiment of FIG. 2, the LED array 15 may include a rectangular grid of 144 LEDs, for example. The present invention is not limited to this specific LED array 15, and may feature less or more than this specific number of LEDs or any non-rectangular grid of LEDs in an array that is used to illuminate the region 18 of the body 14, provided that the number of LEDs used in the array is sufficient to illuminate the region 18 of the body 14 with sufficient power to cause the desired effect.

Figure 4:
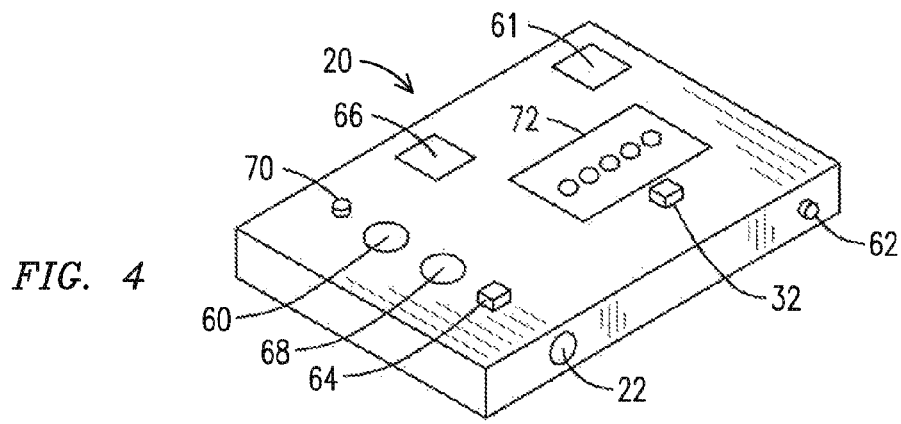
FIG. 4 is a perspective view of a controller used in the system of FIG. 1 to control the array of LEDs of FIG. 3.
Figure 5:
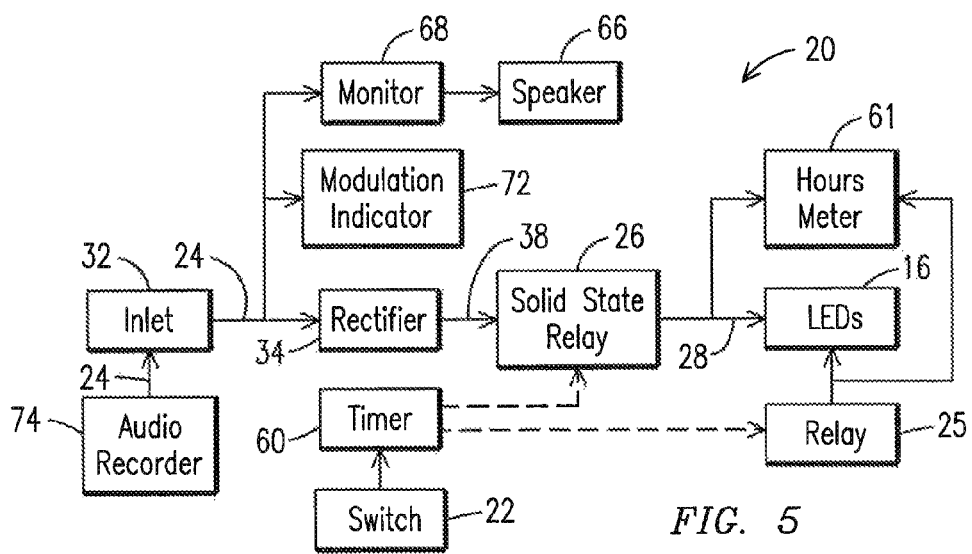
FIG. 5 is a block diagram illustrating connections between components of the controller of FIG. 4.

FIGS. 4-5 illustrate the controller 20 of the system 10. In addition to determining the selective peak wavelength, the selective power density and the selective time period of the radiation from the LED array 15 at the region 18 of the body 14, the controller 20 modulates the radiation output from the LED array 15 at a selective frequency to further stimulate the lipolysis in the adipocytes 12 at the region 18 of the body 14. As illustrated in FIG. 4, the controller 20 includes a switch 22 to select between internal modulation or external modulation to modulate the radiation output from the array 15. Additionally, the switch 22 may be moved to an off position, to turn the controller 20 and the LED array 15 off. Modulation of the output of the LED array 15 is not required, but may enhance the removal of lipid content from the adipocytes. For example, if the LED array 15 is positioned at the selective distance 50 from the region 18 of the body 14, so that the energy density at the region 18 of the body 14 exceeds the range needed for lipolysis, modulation of the output of the LED array 15 can reduce the energy density at the region 18 to be within the range need for lipolysis. Indeed, the controller 20 of the present invention is configured to modulate the output of the LED array 15 and to vary the selective distance 50 of the LED array 15 above the region 18, so that the energy density at the region 18 is within the range required for lipolysis.

As illustrated in FIG. 5, when the switch 22 is used to select internal modulation the switch 22 transmits a signal to the timer 60 to initiate a countdown of the selective time period. The timer 60 then transmits a signal to the relay 25, after which the relay 25 sends an input signal 28 to the LED array 15, which is modulated based on an internal modulation signal at a predetermined modulation frequency. The relay 25 also transmits a signal to an hours meters 61, which monitors the elapsed time that the relay 25 outputs the input signal 28 to the LED array 15. As illustrated in FIG. 1, the controller 20 is connected to a power source 59 with a cable 56. In an exemplary embodiment, the power source 59 transmits the input signal 28, which is an AC (alternating current) signal to the relays 25, 26, so that the relays 25, 26 can subsequently transmit the input signal 28 to the LED array 15, subject to internal/external modulation. Additionally, the power source 59 transmits a DC (direct current) signal, to power the components of the controller 20. For example, the input signal 28 from the power source 59 may be a 120V AC signal and the DC signal may be a 12V DC signal, to power the components of the controller 20. The controller 20 may include a 4 A fuse, to protect the operator and the controller 20 in the event of an electrical problem of excessive current flow through the controller 20. In an exemplary embodiment, the input signal 28 is modulated such that the input signal 28 is shut off during negative portions of the internal modulation signal and the input signal 28 is transmitted to the LED array 15 during positive portions of the internal modulation signal. When the switch 22 is used to select internal modulation, the external modulation of the input signal 28 (discussed below) is not active.

Figure 6:
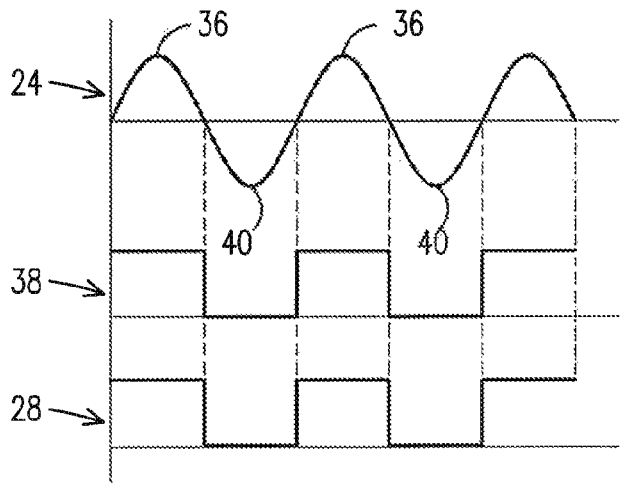
FIG. 6 is a plot of an external modulation signal received at the controller inlet of FIG. 5, a direct current signal transmitted from the rectifier of FIG. 5 and an input signal transmitted from the solid state relay of FIG. 5.

As illustrated in FIG. 5, when the switch 22 is used to select external modulation, an inlet 32 is provided to receive an external modulation signal 24 from an audio recorder 74 at the selective frequency. For example, the external modulation signal 24 may be a digital or analog sound signal from the audio recorder 74, which transmits the external modulation signal 24 to the inlet 32 through a standard ⅜ inch mini-phone plug cable, for example. The inlet 32 passes the external modulation signal 24 to a half-wave rectifier 34. As illustrated in FIG. 6, the half-wave rectifier 34 converts positive portions 36 of the external modulation signal 24 into positive portions of a DC signal 38 and blocks negative portions 40 of the external modulation signal 24 from the DC signal 38, thereby resulting in the DC signal 38 with positive portions corresponding to the positive portions 36 of the external modulation signal 24. As illustrated in FIG. 5, the half-wave rectifier 34 then transmits the DC signal 38 to a solid state relay 26, which subsequently outputs the input signal 28 to the LED array 15 during the positive portions of the DC signal 38 and thereby blocking the input signal 28 to the LED array 15 during the negative portions 40 of the external modulation signal 24. When the switch 22 is used to select external modulation, the internal modulation of the input signal 28 (discussed above) is not active.

As further illustrated in FIG. 4, the controller 20 includes a timer 60 to adjust the selective time period during which the relay 25, 26 transmits the input signal 28 to the LED array 15. Additionally, the controller 20 includes a start button 62 to start the timer 60 and start the transmission of the input signal 28 from the relay 25, 26 to the LED array 15 for the selective time period. Additionally, the controller 20 includes a stop button 64 to stop the timer 60 and stop the transmission of the input signal 28 from the relay 25, 26 to the LED array 15.

When the switch 22 is used to select external modulation of the LED array 15, the controller 20 is also provided with a speaker 66 to output a sound of the external modulation signal 24 received through the inlet 32. Also, the controller 20 features a monitor 68 to control a volume of the sound of the external modulation signal 24 that is outputted through the speaker 66. A different sounding audio output from the speaker 66 will result in the LED array 15 having a different modulation or fluency, resulting in varying photochemical and biochemical responses and outcomes at the cellular level. The system 10 provides maximum flexibility and variation in the modulation signal design and processing. The controller 20 also features an LED indicator 70 to show that the input signal 28 is transmitted to the LEDs 16 and a modulation indicator 72 to show a presence and a signal strength of the external modulation signal 24 received through the inlet 32. In the exemplary embodiment of FIG. 4, the modulator indicator 72 shows the signal strength based on the number of lights of the indicator 72 that are illuminated. However, this specific design is merely exemplary and any modulator indicator design may be provided, as long as it indicates the presence and signal strength of the external modulation signal 24 received through the inlet 32.

The LED array 15 is connected to the controller 20 with the cable 58 and the controller 20 controls the array 15 via specific modulation patterns provided for decreasing the lipid content of adipocytes 12 without permanent or adverse effects on the adipocytes 12 and their surrounding tissues. In an exemplary embodiment, the LED array 15, in conjunction with its modulation by the controller 20, can be used to direct light at the epidermis 42, dermis 44 and the underlying adipose tissue 46 by applying radiation of a dominant peak wavelength of 635 nm in order to affect specific cellular enzymatic processes, such as pain reduction, lipolysis, stimulation of production of collagen, elastin, leptin, and adiponectin. As previously discussed, the input signal 28 to the LED array 15 is modulated in accordance with a selective frequency which may be internally or externally modulated and may vary with respect to time. For example, when external modulation is used, the LED array 15 emits radiation when the external modulation signal 24 is positive and does not emit radiation when the external modulation signal 24 is at or below zero, thereby varying the fluency of the radiation from the LED array 15. The selective frequency is detected with the rectifier 34 and the input signal 28 is transmitted by the high-speed, solid state relay 26 to the LED array 15, so that the input signal 28 is on during the positive portions 36 of the external modulation signal 24 and the input signal 28 is off during the negative portions 40 of the external modulation signal 24. However, this is merely an exemplary modulation design, and the present invention may use any other modulation design, such as the input signal 28 being on during negative portions of the modulation signal and being off during positive portions of the modulation signal or being on during a first cycle of the modulation signal and being off during a second cycle of the modulation signal, for example. Indeed, any modulation design may be used for the input signal 28, provided that the LED array 15 output enhances the removal of lipid content from the adipocytes 12. Table 1 below provides examples of various specific selective frequencies of the external modulation signal 24:

|  | Frequencies | | | | | | | |
| --- | --- | --- | --- | --- | --- | --- | --- | --- |
|  | U | A | B | C | D | E | F | G |
| Value (Hz) | 1.14 | 2.28 | 4.56 | 9.125 | 18.25 | 36.5 | 73 | 146 |
| Harmonic (Hz) |  | 292 | 584 | 1168 | 2336 | 4672 | 9344 | 18688 |

The harmonic selective frequencies A-E in Table 1 above may be used for the external modulation signal 24, since these selective frequencies may be particularly advantageous in regard to removal of lipid content from the adipocytes 12 during lipolysis and pain reduction when the region 18 of the body 14 is illuminated with the LED array 15. In one example, each specific numerical harmonic frequency (which is approximately $128^{th}$ order harmonics of the base frequencies in Table 1) may be used for specific treatments, such as pain reduction (harmonic frequencies E and G) and lipolysis (harmonic frequencies A, B and F). However, although Table 1 provides specific numerical modulation frequencies for the external modulation signal 24, these numerical frequencies are merely exemplary and the selective frequency of the external modulation signal 24 may be varied to be within +/−30% of these numerical frequencies in Table 1, for example. Furthermore, the selective frequency of the external modulation signal 24 used in the present invention may be any numerical frequency other than these specific numerical frequencies in Table 1, provided that the external modulation of the LED array 15 enhances the removal of lipid content from the adipocytes 12.

Figure 7A:
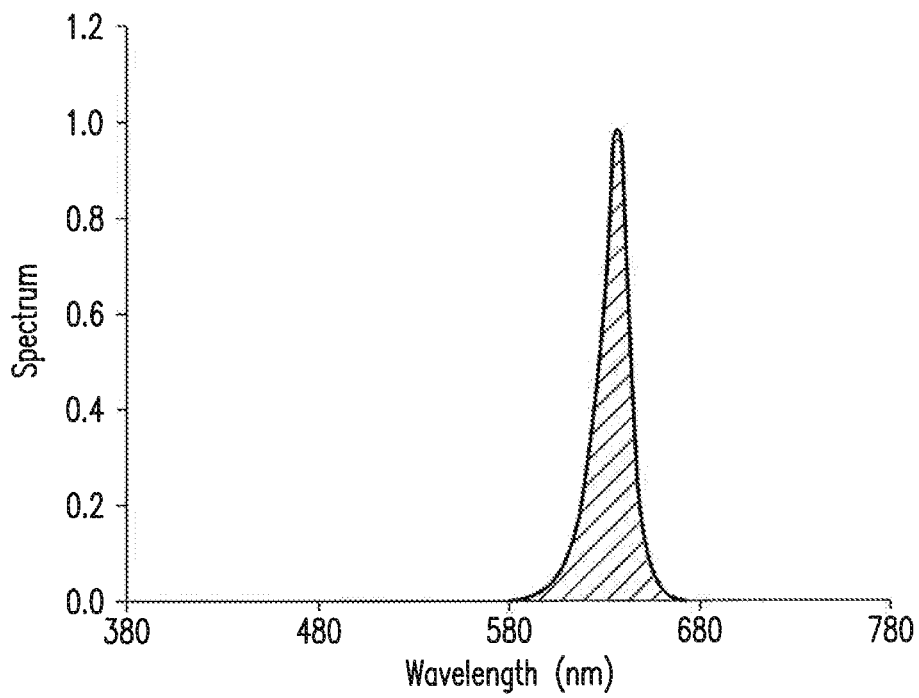
FIG. 7A and FIG. 7B is a plot of spectral output and a chromaticity diagram of the array of FIG. 3.
Figure 7B:
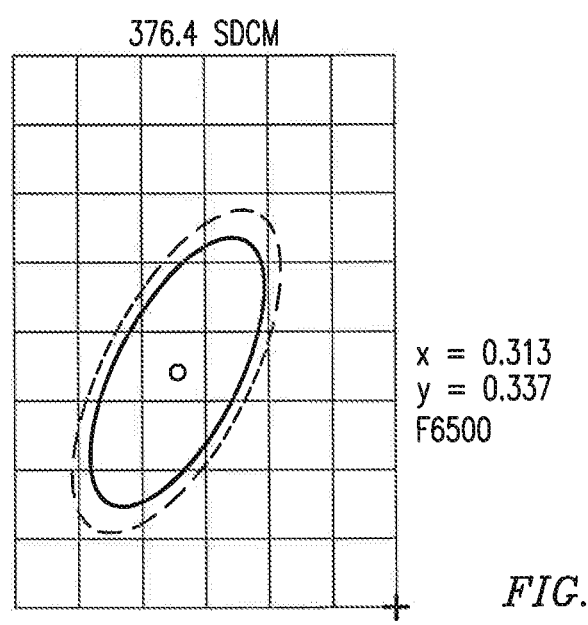

FIGS. 7A and 7B illustrate an exemplary embodiment of a spectral plot and a chromaticity diagram of the LED array 15. Table 2 provides sample data of this spectral plot and chromaticity diagram:

Color Parameters:

Chromaticity Coordinate: x = 0.6983 y = 0.2941/u' = 0.5442 v' = 0.5157
Tc = 1001K Dominant WL: Ld = 634.1 nm Purity = 97.7%

-continued

Ratio: R = 98.4% G = 1.6% B = 0.0% Peak WL: Lp = 637.2 nm
HWL = 16.5 nm
Render Index: Ra = 17.2

R1 = 10 R2 = 82 R3 = 33 R4 = −21 R5 = 7 R6 = 94 R7 = 4
R8 = −72 R9 = −229 R10 = 77 R11 = −3 R12 = 77 R13 = 36
R14 = 61 R15 = 033
Photo Parameters:

Flux = 62.85 lm Eff.: 37.25 lm/W Fe = 394.1 mW
Electrical Parameters:

VF = 2.812 V IF = 599.9 mA P = 1688 mW
IR = 0 uA (VR = 5.006 V)

Although FIGS. 7A and 7B and Table 2 provide sample data of the LED array 15 used in the system 10 according to one exemplary embodiment of the present invention, the system 10 of the present invention is not limited to using an LED array 15 with these specific numeric parameters. Additionally, the system 10 of the present invention is not limited to any specific array of LEDs 16, nor limited to the use of LEDs as the optical device that is used to illuminate the region 18 of the body 14, provided that the optical device of the system 10 that is used provides a sufficient energy density that stimulates lipolysis in the adipocytes 12 at the region 18 of the body 14.

Figure 8:
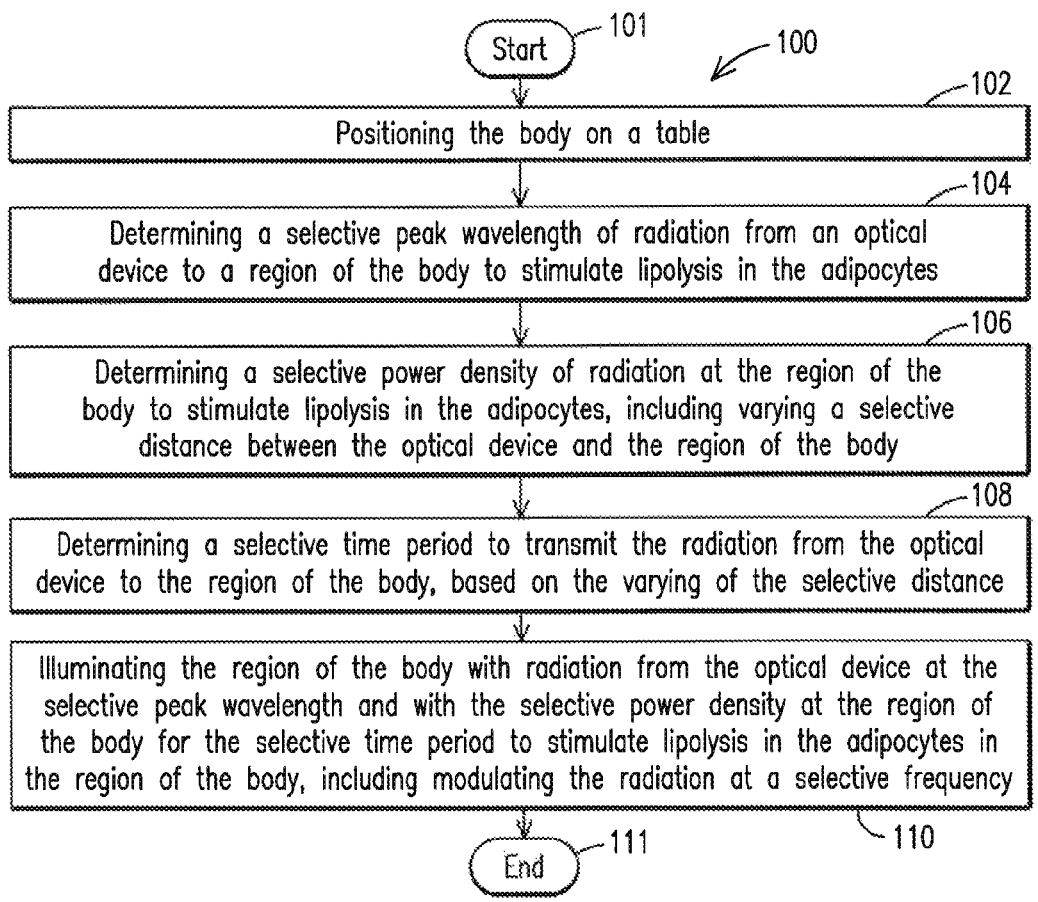
FIG. 8 is a flowchart depicting a method for reducing lipid content of adipocytes in a body in accordance with the present invention.

FIG. 8 depicts a flowchart of a method 100 for reducing lipid content of adipocytes 12 in the body 14. The method 100 is non-invasive and reduces fat and cellulite in a body 14 by applying optical energy to the selected region 18 of the body 14. The effect of the method 100 is to reduce a circumference in the region 18 of the body 14. The extent to which the circumference of the body 14 is reduced depends on each patient, based on such factors as age, metabolism, food and drink intake, and alcohol consumption. In an exemplary embodiment, the circumference of a waist of the body 14 may be reduced by 5.1 cm during one treatment session, for example. In an exemplary embodiment, the photonic energy of the radiation from the LEDs 16 is sufficient to reduce visceral fat deposits of obese patients as well as subcutaneous fat in subjects. As appreciated by one skilled in the art, subcutaneous fat is positioned underneath the skin layer, but over the muscle wall, whereas visceral fat is positioned behind the muscle wall, surrounding internal organs. The method 100 begins at 101 by positioning 102 the region 18 of the body 14 on the table 52 and determining 104 a selective peak wavelength of radiation from the LED array 15 to the region 18 of the body 14 to stimulate lipolysis in the adipocytes 12 in the region 18 of the body 14. The method 100 also includes determining 106 a selective power density of radiation at the region 18 of the body 14 to stimulate lipolysis in the adipocytes 12, including varying the selective distance 50 between the LED array 15 and the region 18 of the body 14. The method 100 also includes determining 108 a selective time period to transmit the radiation from the LED array 15 to the region 18 of the body 14, based on the varying of the selective distance 50. The method 100 also involves illuminating 110 the region 18 of the body 14 with radiation from the LED array 15 at the selective peak wavelength and with the selective power density at the region 18 of the body 14 for the selective time period to stimulate lipolysis in the adipocytes 12 in the region 18 of the body 14, where the illuminating 110 step involves modulating the radiation at a selective frequency, before the method ends at 111.

The advantages of the present invention may include, without limitation, the stimulation of biochemical processes of lipolysis and other desirable effects in the adipocytes 12, which may reduce obesity, and reduce harmful side effects of obesity, such as diabetes, high blood pressure, and heart attacks. Other benefits of the present invention may include pain reduction and the stimulation of production of collagen, elastin, leptin, and adiponectin, as well as the reduction of blood triglycerides as a side effect of lipolysis of the adipocytes. The system 10 may result in a reduction in lipid content of adipocytes 12, which can reduce the BMI of obese individuals. Additionally, the system 10 may significantly reduce healthcare costs for those individuals who would otherwise require treatment for the typical side effects of obesity. In addition, the noninvasive and non-painful system 10 offers significant advantages over a surgical method of lipid reduction in the adipocytes 12. Further, many obese individuals are not surgical candidates and thus would not have this alternative available as an option.

In one embodiment, the present invention is an optical device such as the LED array 15 that can be used to illuminate the skin and underlying subcutaneous fat deposits, causing a photochemical reaction that stimulates specific cellular processes, such as lipolysis and freeing of cellular triglycerides and a reduction of blood triglycerides as a side effect of lipolysis of the adipocytes, pain reduction, as well as stimulation of collagen and elastin production, among other beneficial effects. In one embodiment, an optical illumination device such as the LED array 15 may operate at a wavelength centered around the 635 nm wavelength. Lipolysis refers to the biochemical breakdown and release of stored fat from adipose tissue 46. Lipolysis of triacylglycerol stores located in white adipose tissue results in the liberation of glycerol and nonesterified fatty acids that are released into the vasculature for use by other organs as energy substrates. Lipolysis rates are usually precisely regulated through hormonal and biochemical signals. These signals modulate the activity of lipolytic enzymes and accessory proteins, allowing for maximal responsiveness of adipose tissue to changes in energy requirements and availability. These signals modulate the activity of lipolytic enzymes and accessory proteins, allowing for maximal responsiveness of adipose tissue to changes in energy requirements and availability.

The system 10 may be a Light Stimulated Adipocyte Depletion (LSAD) device, and be used to stimulate biochemical signals to cause lipolysis irrespective of changes in energy requirements and availability. The system 10 may also affect systemic and local controls of enzymatic modulation over biochemical hydrolysis (lipolysis) and synthesis (lipogenesis) of triacylglycerol. Triacylglycerol, which is metabolically active, is typically hydrolyzed to release the fatty acids from the adipocytes 12. This occurs on a continual basis, where stores are continually being hydrolyzed and resynthesized. Adipocytes 12 are typically found mostly in the abdominal cavity and subcutaneous tissue.

Leptin has a central role in the metabolism of adipocytes 12. Leptin coordinates intricate biological processes through its receptors. Leptin deficiency or leptin resistance can result in obesity, diabetes, and infertility in humans. Leptin has broad effects on angiogenesis, blood pressure, bone mass, hematopoiesis, lymphoid organ homeostasis, reproduction, and T lymphocyte systems. Leptin circulating in the blood regulates energy intake and energy expenditure via, its control of appetite and metabolism. The level of circulating leptin is directly proportional to the total amount of adipocytes in the body. The system 10 may be used as an LSAD device to modulate the biochemistry of adipocytes to affect leptin production and therefore, facilitate fat reduction. According to the system 10, light centered around the 635 nm wavelength, with sufficient Power Density (W/cm2), temporal characteristics, and Energy Density (fluence or J/cm2) according to LSAD, increases the amount of Leptin that is produced by the adipocytes 12, since leptin production is a side effect of the lipolysis of the adipocytes 12. This may be a valuable effect that assists in fat reduction and weight loss.

The system 10 may be used as a LSAD device to alter enzymatic processes at the membrane level to produce an acceleration of lipolysis. The system 10 alters cellular structures, the extra cellular matrix, transmembrane "integrin receptors," and cytoskeletal structures; specifically the membrane of the adipocyte 12, to allow lipids to leak to interstitial space and be metabolized by the body 14. During the illumination of the region 18 of the body 14 with the LED array 15, no significant heat or detrimental effects to the region 18 are produced.

The epidermis layer 42 of FIG. 2 is the outermost layer of the skin and forms the waterproof, protective wrap over the body 14 surface. The dermis layer 44 is the layer of skin beneath the epidermis 42 that consists of connective tissue. In an exemplary embodiment, collagen is the main component of connective tissue, and is the most abundant protein in mammals, making up about 25% to 35% of the whole-body protein content, for example. The dermis layer 44 constitutes about 15 to 20% of the weight of the body 14. At many different wavelengths of light, only a single tissue constituent (e.g., water or collagen) absorbs the energy from the light. Therefore, it is important that the controller 20 determine the selective peak wavelength so that it can be transferred through the dermis layer 44 to the subcutaneous adipose tissue 46. Due to the characteristics of skin components, the distribution of optical radiation through the epidermis 42 and dermis 44 to the subcutaneous adipose tissue 46 is controlled by various factors including the selective time period of exposure, absorption and scattering properties of layers of skin on the body 14, and the selective power density of the LED array 15 and the selective frequency used to modulate the LED array 15. These factors are used by the controller 20 to determine proper energy penetration through the skin layers 42, 44, 46 to the subcutaneous adipocytes 12 at the subcutaneous adipose tissue 46. Thus, optical absorption, refraction and scattering are factors considered by the controller 20 in determining the selective power density and selective energy density of the LED array 15 at the region 18 of the body 14 and/or at the subcutaneous adipose tissue 46. Because the dermis 44 possesses significant amounts of collagen fibrils, a significant amount of optical scattering may occur at the dermis layer 44. The scale and degree of light absorption in the skin is relative to the scattering that takes place during the radiation of the skin. The selective peak wavelength and the selective power density are determined by the controller 20 in order to safely augment a cell's existing biochemical and enzymatic processes.

Photons that enter skin tissue at the region 18 of the body 14 are scattered one or more times until they either escape or are absorbed. The Beer-Lambert Law is applied if absorption (rather than scattering) is dominant in the skin tissue. The Beer-Lambert law describes the logarithmic dependence between the transmission, T, of light through a substance and the product of the absorption coefficient of the substance, $\alpha$, and the distance the light travels through the tissue (i.e., the path length), l. The spatial distribution of the absorbed radiation in a tissue from a known absorption coefficient of a particular wavelength can thereby be determined. If scattering prevails over absorption, then a stochastic analysis may be used to determine the selective power density of the absorbed radiation for particular wavelengths, such as those used in the system 10. In an exemplary embodiment, the adipocytes 12 in the subcutaneous adipose tissue 46 begin at a depth of approximately 4 mm or greater into the skin at the region 18 of the body 14, and may be deeper for some individuals or some body regions. In addition, the cellular structure of the skin at the region 18 of the body 14 may vary due to differences in individual chemistries, hydration of the skin, and existence of collagen fibrils of varying densities, lengths, and thicknesses. Therefore, various power densities of the LED array 15 of the system 10 may be applied to achieve desired results according to the present invention. In an exemplary embodiment, the output power of the LED array 15 will be of a level such that the power density (W/cm2) of the radiation at the region 18 of the body 14 will be sufficient to cause the optical energy that penetrates the dermis 44 to be of greater energy density and/or greater power density at the depth of the adipose tissue 46 than it is at the surface of the epidermis 42.

The LED array 15 and/or the controller 20 may be provided with a power limiter to limit the dosage of applied illumination to any particular patient, for example. The selective power density and/or selective energy density at the region 18 of the body 14 and distribution at the adipose tissue 46 under the skin that is maintained with less energy and power and without any significant thermal rise to the dermal layer 44. The system 10 provides:

1) The selective power density and/or energy density at the adipose tissue 46 is greater than the power density and/or energy density at the epidermis layer 42 at the region 18 of the body 14;

2) The region 18 of the body 14 is based on the area of illumination of the LED array 15 and makes use of the effects of Optical Energy Tissue distribution phenomena to effect a reduction in lipid content of adipocytes 12 in adipose tissue 46 while also stimulating positive biochemical and photochemical effects in the epidermis 42 and dermis 44 layers.

The system 10 may utilize LSAD techniques that illuminate the region 18 of the body 14 with the LED array 15 at predetermined power densities and time periods that thermodynamically lower enzymatic transition states of necessary enzymes in the adipocytes 12, via the absorption of optical energy at a selected wavelength of about 635 nm in the lipid bilayer, and in the lipid pool, hence stimulating positive biochemical processes in these cells. The system 10 parameters, including the selective peak wavelength (such as 635 nm, for example), an output power of the LED array 15 (in watts), and the selective time period (in minutes) to achieve the desired outcome. Additionally, the system 10 parameters include modulation parameters, including whether the system 10 will use external or internal modulation, for example, and the selective frequency of the modulation signal. These parameters, combined with the area of the region 18 of the body 14 at the treatment surface being selected, may determine the selective power density at the region 18 of the body 14 (and at the adipose tissue 46) to reduce the lipid content of the adipocytes 12.

Biochemical processes modulated by the system 10 of the present invention include but are not limited to lipolysis, lipogenesis, leptin production, and glucose absorption or metabolism. This can result in the reduction of cellular levels of triglycerides as well as a reduction of blood triglycerides, as a side effect of lipolysis of the adipocytes, in addition to reduced levels of low density lipoprotein (LDL), for example.

According to the first law of photochemistry, the Grotthuss-Draper law, in order for a photochemical reaction to take place, light is absorbed by a compound. Thus, if light of a particular wavelength is not absorbed by a skin layer, no photochemistry will occur, nor photobiological effects, no matter how long one irradiates the skin layer with that non-absorbed wavelength of light. Once a given photobiological response is observed at an absorbed wavelength, the controller 20 determines the optimum dose of the absorbed wavelength of light needed to produce the desired photobiological response. Upon determining the optimum dose of each absorbed wavelength, the controller 20 determines the relative effectiveness of different absorbed wavelengths of light at different power densities/energy densities, in order to cause the desired biological response, such as reduction of lipid content in the adipocytes 12, for example. Enhanced lipolysis is the result of photochemical and/or photophysical changes produced by the absorption of the selective peak wavelength (determined by the controller 20) at proper power densities and/or energy densities.

This written description uses examples to disclose embodiments of the invention, including the best mode, and also to enable any person skilled in the art to make and use the embodiments of the invention. The patentable scope of the embodiments of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:
   an optical device configured to illuminate a region of a body at a selective peak wavelength in a range between 630-660 nm and at a selective power density for a selective time period to reduce lipid content of adipocytes in the body; and
   a controller connected to the optical device to determine the selective wavelength, the selective power density and the selective time period to stimulate lipolysis in the adipocytes,
   wherein said optical device is further configured to be located at a distance away and separate from the region of the body.

2. The system of claim 1, wherein the optical device is an array of LEDs, wherein the selective peak wavelength is approximately 635 nm, and wherein the controller is further configured to modulate an output of the LEDs at a selective frequency to stimulate the lipolysis in the adipocytes and wherein the selective frequency is one of 2.28 Hz, 4.56 Hz and 73 Hz.

3. The system of claim 2, wherein the controller includes:
   a switch to select between an internal modulation signal or an external modulation signal to modulate the LEDs; and
   a relay to transmit an input signal to the LEDs at the selective frequency based on one of the internal modulation signal or the external modulation signal.

4. The system of claim 3, wherein upon said switch being used to select the external modulation signal, said controller includes:
   an inlet for receiving the external modulation signal at the selective frequency;
   a half-wave rectifier to convert positive portions of the external modulation signal into a direct current signal and to block negative portions of the external modulation signal; and
   the relay is a solid state relay to receive the external modulation signal and to output the input signal to the LEDs during the positive portions of the direct current signal.

5. The system of claim 1, wherein said selective wavelength, said selective power density and said selective time period are determined to stimulate lipolysis in the adipocytes in the body with a body mass index in excess of 30.

6. The system of claim 1, wherein said selective wavelength, said selective power density and said selective time period are determined to penetrate an epidermis, a dermis and an underlying adipose tissue of the region of the body to a depth range of 8-10 mm.

7. The system of claim 1, wherein said selective power density on the region of the body is in a range between 75-1500 mW/cm$^2$; wherein said selective time period is in a range between 6-120 minutes; wherein said optical device is configured to illuminate the region of the body at a selective energy density in a range between 4-82.5 J/cm$^2$; and wherein the distance away and separate from the region of the body of the optical device is in a range of 2.5-45.7 cm.

8. The system of claim 1, wherein said controller is configured to vary a selective distance between the optical device and the region of the body, wherein the optical device is an array of LEDs, wherein the selective peak wavelength is approximately 635 nm, wherein the selective time period is approximately 8 minutes, and wherein the selective distance is approximately 20.3 cm.

9. The system of claim 1, wherein said controller is configured to vary a selective distance between the optical device and the region of the body and wherein said selective distance is in a range of 2.5-45.7 cm.

10. The system of claim 8, wherein said system further comprising:
    a support configured to hold the region of the body in a stationary position; and
    an adjustable stand configured to hold the optical device at the selective distance above and separate from the region of the body, wherein the controller is connected to the adjustable stand and is configured to transmit a signal to the adjustable stand to vary the selective distance.

11. The system of claim 4, wherein the controller includes:
    a timer to adjust the selective time period during which the relay is configured to transmit the input signal to the LEDs;
    a start button to start the timer and start the transmission of the input signal from the solid state relay to the LEDs for the selective time period; and
    a stop button to stop the timer and stop the transmission of the input signal from the solid state relay to the LEDs.

12. The system of claim 4, wherein the controller includes:
    a speaker to output a sound of the external modulation signal received through the inlet;
    a monitor to control a volume of the sound of the external modulation signal through the speaker;
    an LED indicator to show that the input signal is being transmitted to the LEDs; and
    a modulation indicator to show a signal strength of the external modulation signal received through the inlet.

13. The system of claim 4, further comprising an audio recorder connected to the inlet, said audio recorder to transmit the external modulation signal to the inlet, wherein said external modulation signal is one of an analog or digital audio signal.

14. A system for reducing pain in a body, said system comprising:
    a support to hold a region of the body in a stationary position;

an array of LEDs configured to output a peak wavelength with a selective power density at the region of the body for a selective time period sufficient to reduce pain in the region of the body;

a stand to hold the array of LEDs at a selective distance in a range of 2.5-45.7 cm away and separate from the region of the body; and a controller connected to the LEDs and the adjustable stand, said controller configured to transmit a signal to one of the stand or the support to vary the selective distance, and said controller configured to modulate an output of the LEDs at a selective frequency based on a transmission of an input signal to the LEDs at the selective frequency, wherein the selective frequency is based on one of an internal modulation signal or an external modulation signal.

15. The system of claim 14, wherein the support is a table, wherein the stand is adjustable based on the controller being configured to transmit the signal to the stand and wherein said controller includes:

a switch to select between one of the internal modulation signal or the external modulation signal to modulate the input signal to the LEDs;

a relay to transmit the input signal to the LEDs at the selective frequency based on one of the internal modulation signal or the external modulation signal.

16. The system of claim 15, wherein said switch being used to select the external modulation signal, said controller further includes:

an inlet for receiving the external modulation signal at the selective frequency;

a half-wave rectifier to convert positive portions of the external modulation signal into a direct current signal and to block negative portions of the external modulation signal; and the relay is a solid state relay to receive the external modulation signal and to output the input signal to the LEDs during the positive portions of the direct current signal.

17. The system of claim 15, wherein upon said controller varying the selective distance, the controller is configured to vary the selective time period to reduce pain in the region of the body; wherein upon increasing the selective distance, the controller is configured to increase the selective time period; and wherein upon decreasing the selective distance, the controller is configured to decrease the selective time period.

18. A method for reducing lipid content of adipocytes in a body, said method comprising:

positioning a region of the body in a stationary position with a support;

determining a selective peak wavelength of radiation in a range of 630-660 nm from an optical device to the region of the body to stimulate lipolysis in the adipocytes in the region of the body;

determining a selective power density of radiation at the region of the body in a range between 75-1500 mW/cm$^2$ to stimulate lipolysis in the adipocytes, including varying a selective distance in a range of 2.5-45.7 cm between the optical device and the region of the body;

determining a selective time period in a range of 6-120 minutes to transmit the radiation from the optical device to the region of the body, based on the varying of the selective distance; and illuminating the region of the body with radiation from the optical device at the selective peak wavelength and with the selective power density at the region of the body for the selective time period to stimulate lipolysis in the adipocytes in the region of the body, including modulating the radiation at a selective frequency.

19. The method of claim 18, wherein said modulating the radiation at selective frequency includes:

receiving an external modulation signal at the selective frequency;

converting positive portions of the external modulation signal into a direct current signal;

blocking negative portions of the external modulation signal; and outputting an input signal to the optical device to illuminate the region of the body during the positive portions of the external modulation signal.

20. The method of claim 18, wherein the illuminating step is to further reduce cellular levels of triglycerides and reduce blood triglycerides, as a side effect of the lipolysis in the region of the body.

21. The system of claim 14, wherein the selective peak wavelength is in a range between 630-660 nm; wherein said selective power density on the region of the body is in a range between 75-1500 mW/cm$^2$; wherein said selective time period is in a range between 6-120 minutes; wherein said selective frequency is one of 36.5 Hz and 146 Hz and wherein said optical device is configured to illuminate the region of the body at a selective energy density in a range between 4-82.5 J/cm$^2$.

* * * * *